United States Patent [19]

Harju-Jeanty et al.

[11] Patent Number: 5,651,975
[45] Date of Patent: Jul. 29, 1997

[54] METHOD FOR THE PREPARATION OF HERBICIDAL GRANULAR PRODUCTS COMPRISING TWO SEPARATE PHASES

[76] Inventors: Pontus Harju-Jeanty, Almantie 24, FIN-65610 Mustasaari; Ari Juppo, Isolahdentie 4 as. 6, FIN-65210 Vaasa, both of Finland

[21] Appl. No.: 601,842

[22] Filed: Feb. 15, 1996

Related U.S. Application Data

[63] Continuation of Ser. No. 211,282, filed as PCT/FI92/00258, Sep. 25, 1992, published as WO93/05652, Apr. 1, 1993, abandoned.

[30] Foreign Application Priority Data

Sep. 27, 1991 [FI] Finland ............................ 914545

[51] Int. Cl.$^6$ ................................................ A01N 25/32
[52] U.S. Cl. ...................... 424/406; 424/409; 424/419; 424/420
[58] Field of Search ............................ 424/405–409, 424/417–421

[56] References Cited

U.S. PATENT DOCUMENTS

| | | | |
|---|---|---|---|
| 3,692,820 | 9/1972 | Boroschewski et al. | 260/472 |
| 3,920,442 | 11/1975 | Albert et al. | 71/92 |
| 4,197,112 | 4/1980 | Albert et al. | 71/111 |
| 4,386,101 | 5/1983 | Drabek et al. | 424/285 |
| 4,557,751 | 12/1985 | Ronning et al. | 71/91 |
| 4,867,972 | 9/1989 | Girardeau et al. | 424/81 |
| 5,230,892 | 7/1993 | Feyen et al. | 424/409 |

FOREIGN PATENT DOCUMENTS

| | | |
|---|---|---|
| 679283 | 10/1966 | Belgium. |
| 1282608 | 4/1991 | Canada. |
| 2051346 | 3/1992 | Canada. |
| 107107 | 5/1984 | European Pat. Off.. |
| 201417 A1 | 11/1986 | European Pat. Off.. |
| 201417 | 11/1986 | European Pat. Off.. |
| 224845 | 6/1987 | European Pat. Off.. |
| 257686 | 3/1988 | European Pat. Off.. |
| 413267 | 2/1991 | European Pat. Off.. |
| 465889 | 1/1992 | European Pat. Off.. |
| 473003 | 3/1992 | European Pat. Off.. |
| 476555 | 3/1992 | European Pat. Off.. |
| 15 67 164 | 3/1985 | Germany. |
| 40 24 436 | 2/1991 | Germany. |
| 630508 | 6/1982 | Switzerland. |
| 1193998 | 6/1970 | United Kingdom. |
| 2234678 | 2/1991 | United Kingdom. |
| 2245494 | 1/1992 | United Kingdom. |
| WO 91/13546 | 9/1991 | WIPO. |

*Primary Examiner*—Neil S. Levy
*Attorney, Agent, or Firm*—Marshall, O'Toole, Gerstein, Murray & Borun

[57] ABSTRACT

The invention relates to a method of producing granular mixtures which contain herbicides known per se, the activator used being a solid composition in which the activator ingredients are either impregnated into and/or mixed with a carrier material.

16 Claims, No Drawings

METHOD FOR THE PREPARATION OF HERBICIDAL GRANULAR PRODUCTS COMPRISING TWO SEPARATE PHASES

This is a continuation of U.S. application Ser. No. 08/211,282, filed as PCT/FI92/00258, Sep. 25, 1992, published as WO93/05652, Apr. 1, 1993, now abandoned.

The present invention relates to a method of producing herbicidal granular products which contain carbamoyloxyphenylcarbamates and/or substituted benzofuranes, known per se, as active ingredients, surfactants, suspending agents, inert carriers, and possibly other auxiliary agents, such as stabilizers, defoamers, coloring agents, and preservatives. The said active ingredients are insoluble in water and in the main foliage-acting, and they are thus sprayed, as water dilutions, onto the plant stand. For this reason the granules are made water dispersible so that a homogenous suspension which will not clog the sprayer will be obtained when the product is diluted with water.

Carbamoyloxyphenylcarbamate and benzofurane herbicides have conventionally been formulated as emulsion concentrates in which the active ingredient is dissolved in organic solvents and can, with the help of solution emulsifiers, be caused to mix with water to form an emulsion. These formulations have, however, the drawbacks of toxicity of the products, due to the organic solvents, inflammability of the products, as well as difficulty of obtaining a stable uncrystallizing emulsion of the product together with water. Crystallization is typical specifically of methyl-3-tolylcarbamoyloxyphenylcarbamate.

Product forms in which the active ingredients are not in a dissolved form are as such advantageous, since then the problems of toxicity, inflammability, packaging material, and storage are usually avoided, since especially in the case of foliage-acting herbicides, penetration and translocation abilities are required in order to achieve sufficient biologic efficacy. Hydrolytic decomposition is often also a disadvantage. An active ingredient in molecular form is, in a true liquid, capable of penetrating through the wax and cuticle layers much more effectively than is a solid particle. For this reason, insoluble particles of the active ingredient must be as finely ground as possible, and their penetration and translocation abilities must be improved with oils, organic solvent additions, and surfactants. In the case of carbamoyloxyphenylcarbamates in particular, it is indispensable to add exceptionally large amounts of these auxiliary agents in order to achieve a sufficient biologic efficacy. Air-jet and suspension mills are used for the grinding to produce a maximally finely divided active ingredient, preferably in the order of magnitude of 1–5 microns, in order to achieve biologic efficacy and as stable a suspension as possible when the granule is dispersed into water.

In solid form, the active ingredient may be present in a water dilutable formulation either as a liquid suspension concentrate or as a granular product dispersible in water. The disadvantages of a liquid product form often include storage difficulties, handling problems due to high viscosity, and the residues remaining in incompletely emptying containers. The last-mentioned disadvantage is becoming a significant environmental problem when the used containers are being disposed of. These problems are avoided with solid granules dispersible in a liquid. In addition, a granular product can be packaged in materials, such as carton, which load the environment less, and thus the empty packages are easier to dispose of.

The basic properties of water-dispersible granules include, in addition to the chemical stability of the active ingredients, also a good ability to be dispersed into water, sufficient granule strength so that detrimental dust is not detached in connection with storage or handling, free flow of the granules, and an ability to remain uncaked during storage. In order to achieve these properties, the granule may contain, in addition to a water-insoluble carrier, also dispersing, suspending, wetting, preserving, defoaming, and anti-caking agents.

It is known that carbamoyloxyphenylcarbamates, the most notable of which are methyl-3-m-tolylcarbamoyloxyphenylcarbamate, generally named phenmedipham, and ethyl-3-phenylcarbamoyloxyphenylcarbamate, generally named desmedipham (BP 679, 283),

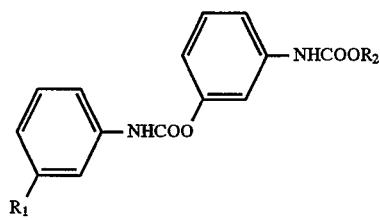

where R1 and R2=CH3 or R1=H and R2 =CH2CH, are selective and good by their herbicidal properties. These active ingredients can be used separately or as mixtures together with each other and/or with other control agents, especially for weed control in sugar beet cultivation.

Conventionally the above active ingredients have been formulated as emulsion concentrates. But since the aim is to avoid organic solvents, and since phenmedipham tends to crystallize when these formulation forms are diluted with water, the object has now been to produce water-dispersible granules of these active ingredients. It is previously known to prepare water-dispersible granules from herbicides (U.S. Pat. No. 3,920,442), as also dispersible triazine herbicidal granules, which contain a surfactant which improves the crystallization properties (U.S. Pat. No. 4,197,112), or granules the physical properties of which are improved by surfactants (EP 201,417). The obstacle to the commercialization of dispersible carbamoyloxyphenylcarbamates has been the difficulty of incorporating sufficient biologic efficacy into the product, since the amount of liquid oil and/or surfactants is very high in ratio to the amounts of the active ingredients (approx. 1:1) and uneconomical to implement technically.

It is known that a good biologic efficacy can be achieved with water dispersible granules made of certain active ingredients of herbicides. However, with carbamoyloxyphenylcarbamates, sufficient efficacy cannot be reached by these methods.

Now it has been observed surprisingly that, with water dispersible granular products which contain carbamoyloxyphenylcarbamate, it is possible not only to achieve the above properties of a granular product but also to enhance them significantly by preparing a granular or tablet-form product in which an activator is impregnated into a carrier, which for its part is added, evenly distributed or as a layer on the surface of the granule or the tablet or as a core inside the granule or the tablet. On the other hand, a separate granule or tablet can be made of a liquid activator and the carrier. The granules, mixed together with granules containing the active ingredient, can be packaged in one container, in one space within it, as a sufficiently evenly distributed granular mix to form one product, or can be used as a separately dispensed agent in a tank mixture. A separate tablet can be dispensed together with a granular or tablet-form active ingredient to form a combined mixture for use.

By using an activator impregnated into a carrier, the enhancing of the biologic efficacy of solid carbamoyloxyphenylcarbamate has even been increased as compared with unimpregnated activator; this has been observed in both greenhouse and field tests.

As the carrier for the activator it is possible to use inorganic substances which adsorb large amounts of oily substances and are of natural origin, such as silica-based substances, aluminum oxide based substances, attapulgite, montmorillonite, mica-based substances, diatomite, bentonite, talcum, kaolin, lime, gypsum, and water-insoluble or water-soluble salts.

On the other hand, it is possible to use as the carrier porous organic substances of natural origin, such as ground wood or corn cobs, ground coconut or almond shells, ground olive skins, ground grain husks, cellulose, starch and alginates, or porous structures which are based on polymeric initial substances of natural origin which have been modified, such as lignin derivatives, cellulose derivatives, starch derivatives, and cyclodextrins, or synthetic polymers such as polyacrylates, polyacryiamides, polyvinyl derivatives, polymers of maleic acid, polyurethanes, polylactides, and polymers of glycolic acid.

The activator may be enclosed in the carrier material by coating the impregnated particles with a polymer, such as polyvinyl alcohol, or with sugar based or sugar alcohol based substances, such as lactose, CMC and sorbitol. In this case the speed of release of the activator can also be regulated.

A liquid activator can also be enclosed in capsules, which can further be used in a granular product. Encapsulation methods are commonly known. The strength of the granules and their resistance to abrasion can also be affected by means of coating materials. On the other hand, the flow of the product can be improved by them.

An activator which contains surfactants and/or oil is not important for the actual granulation; its main purpose is to enhance the biologic action of the product.

The proportion of activator may be in general 1–80% of the weight of the granular product, preferably 0.5–5 times the amount of carbamoyloxyphenylcarbamate in the product.

The activator may be in a solid or a liquid state (at 20° C.), in which case it can be impregnated into a carrier or be mixed with the mix to be granulated. Alternatively it may also be impregnated into or be attached to the product in some other manner after the granulation.

The activator may contain anionic, cationic, non-ionic or ampholytic surfactants, or these together with a mineral oil, vegetable oil or animal oil. The proportion of surfactants in the activator may be 2–100%, preferably 50–100%. The proportion of oil may respectively be 0–98%, preferably 0–50%.

The anionic surfactants may be alkyl sulfonates, alkylaryl sulfonates, sulfate ethers, fatty alcohol sulfates, sulfate ester sulfocarboxylic acids and their derivatives, alkylglycerolether sulfonates, sulfoesters, sulfonamides and phosphoric acid mono- and diesters, bile acids and their salts.

The cationic surfactants may be alkylamines or alkylarylamines, alkyl or alkylaryl imidazolines, and alkylaminoamides.

The non-ionic surfactants may be fatty alcohol ethoxylates, fatty acid ethoxylates, alkylaryl ethoxylates, alkyl sugar ethoxylates or alkyl sugar alcohol ethoxylates, alkylamine or alkylarylamine polyglycol ethers, fatty acid amide derivatives, diethanolamides or polydiethanolamides of fatty acids, derivatives of mono-, di-, and triglycerides, acetylene diols, and silicon-based surfactants.

The ampholytic surfactants may be alkyl and alkylaryl betaine derivatives, alkyl and alkylaryl (poly)glycine derivatives, alkylamide and alkylarylamide carboxylates, and alkylamine and alkylarylamine sulfonates. Surfactants which contain fluorine may also be used.

The oily substance may be a mineral oil, preferably having a low viscosity so that it can easily become impregnated into the carrier. On the other hand, the oil must not significantly impede the crop plant. It is, most advantageous to use low-aromatic paraffin oil, e.g. Neutral solvent 150, Exxon. The oily substance may be a vegetable oil or its hydrolysis product, such as soy oil or a fatty acid mixture of soy oil. The oil may also contain phospholipids and sterols.

The oily substance may be of animal origin, in which case it is preferable if the oil contains a large amount of unsaturated fatty acids and their glycerides.

It is a prerequisite for the granulation of the active ingredient, or of the active ingredient and its carrier which contains an activator, or for the granulation of the carrier or the active ingredient or the activator that the material to be granulated is finely divided.

The material can be comminuted, for example, while dry in an air jet mill or as a suspension in a pearl mill. It is essential that the particle size of the solid is on average approx. 10 µm and that of the active ingredient preferably in the order of 5 µm (measured by a Coulter apparatus), in order for the biologic efficacy to be achieved.

In the granulation, auxiliary agents can be used which promote granule formation, re-wetting of the granules, and rapid decomposition and dispersion of the granules at the time the solution for use is being prepared, as well as agents which inhibit the foaming of the solution for use. Since the active ingredient may decompose in a basic solution for use, inorganic or organic pH control agents may be used in the mixture, such as phosphoric acid or its acid salts and citric acid, so that the pH of the solution for use will be below 7, preferably 3.5–5.5.

Auxiliary granulation agents may be used in granules in which the active ingredient and the activator are in the same granule or in separate active-ingredient granules and activator granules.

Agents promoting the decomposition of the granule, which may be polymers such as polyvinyl pyrrolidone and starch and its modified forms, or salts such as ammonium sulfate, or organic water-soluble compounds such as urea, or substances capable of liberating gas, such as carbonates.

As agents improving the suspension of the granules it is possible to use, as is commonly known, dispersants such as phenyl sulfonates, alkylnaphthalene sulfonates and polymerized naphthalene sulfonates, polyacrylic acids and their salts, polyacrylamides, polyalkoxydiamine derivatives, polyethylene oxides, polypropylene oxide, polybutylene oxide, taurine derivatives and their mixtures, and sulfonated lignin derivatives. Dispersants can be used at 0.1–50%, preferably 5–20% of the granular product.

Similar products may also be used as agents promoting granulation, such as polyethylene glycol, in which case it is advantageous to add the activator-containing component at a proportion of 1–20% to the completed granule which contains the active ingredient.

The foaming of a mixture to be prepared for spraying can be controlled with defoamers such as silica-based agents. It is preferable to use such agents at 0–0.5% of the amount of the granular product.

Prior-known methods can be used for the granulation, such as disc granulation, spray drying (e.g. Niro), fluid-bed granulation (e.g. Glatt and Schugi), stir granulation using a vertical mixer (e.g. Fielder) or a blade mixer (e.g. Forberg), extruder granulation (e.g. Nica) or compacting granulation (e.g. Bepex apparatus) or centrifugal granulation (e.g. CF-granulator, Freund Industrial Co), or spray-bed granulation.

The activator may be compressed into a water-dispersible tablet, in which case its size may vary depending on the matrix. Conventional tablet presses include rotation (Mansty) and eccentric tablet presses (Diaf).

It is also possible to use for the granulation and tabletting two or more of the above methods in series. The granule surface can be hardened mechanically by rounding the granule, for example, by using a Spheronizer apparatus (Nica) or by coating the granules with materials suitable for the purpose, as mentioned above.

It is important that the granular product is dried. The product may be dried either in the apparatus-used for the granulation or in a separate apparatus intended for drying (e.g. a fluid-bed drier). It is advantageous if the moisture content of the granular product is below 5%, preferably below 1%.

The granule size of the final product may vary, depending on the granulation method, on average up to 3 mm or considerably higher, in the case of tablets dispersible in water.

It is self-evident that also other control agents can be mixed together with carbamoyloxyphenylcarbamates (such as phenmedipham and desmedipham) to form a granular product. The control agents may be herbicides, agents for plant-disease control, and insecticides, as well as growth control agents.

It is advantageous to use herbicides used particularly in the cultivation of sugar beet, such as ethofumesate, methamitron, chlorodazone, lenasil, pyridate, metholachlorine, trichloroacetic acid, EPTC, quinmerac, cycloate, chlopyralide, fluroxipyr, isocarbimide, propham, trifluraline, alloxydime sodium, cetoxydime, diallate, fluazifop-butyl, triallate, dalapon or propaqizafob.

The products of the invention can be used after the emergence of seedlings of the crop plant, preferably in several rounds of application during the growing season. A suitable amount of active ingredient per one spraying is 0.1–1 kg per hectare, depending on the number of rounds of application.

The invention is described below in greater detail with the help of examples.

Example 1

A separate granular phenmedipham product can be prepared from a raw-material mixture which contains:

| | |
|---|---|
| phenmedipham | 80% |
| lignin sulfonates | 7.4% |
| phenyl sulfonates | 7.0% |
| diatomite | 2.0% |
| kaolin | 3.6% |

The raw materials used for the preparation are pre-ground with an air-jet mill (Alpine) for granulation. The granulation can be carried out by extrusion (Nica), in which case water is mixed with the dry mix at 10% of the mix. The diameter of the openings in the matrix is 1 mm. The extruded mix is cut into granules of approx. 2 mm in length, which can be further rounded in a Spheronizer apparatus. The product is dried in a fluid-bed drier. The product obtained by the method disperses excellently into water.

The suspension can be verified with an experiment in which 1 g of product is dispensed into a 100 ml narrow-tipped graduated test tube containing 100 ml of distilled water (+25° C.). After the wetting of the granules has been noted, the tube is turned 30 times through 180 degrees. Sediment formation is observed for 1 min, 5 min, and 10 min.

In the case of the above-mentioned granules, the amount of sediment separated at 1 min after mixing is 0.05 ml, at 5 min after mixing 0.05 ml, and at 10 min after mixing 0.05 ml.

The average particle size in the suspension, determined using a Coulter LS 130 apparatus, was approx. 2 µm.

For comparison purposes, a determination of the suspension properties was performed on a commercial product called Goltix. The values obtained were: 1 min) 0.01 ml; 5 min) 0.1 ml; and 10 min) 0.18 ml.

Example 2

A separate granular phenmedipham product can be prepared from a pre-ground raw material mixture which contains:

| | |
|---|---|
| phenmedipham | 89% |
| lignin sulfonate derivatives | 7.2% |
| phenyl sulfonates | 3.6% |

The mixture can be granulated by spray drying from a 50% aqueous suspension of the mixture (Nifo). The average size of the granules depends on the size of the apparatus. The granules are round in shape. Determined by the method described above, the suspension results are: 1 min) 0.15 ml; 5 min) 0.9 ml; 10 min) 1.2 ml. The average particle size in the suspension is 3 µm.

Example 3

A separate granular phenmedipham product can be prepared from the raw materials mentioned in Example 1 by using disc granulation, in which case the mix to be granulated is wetted using water at 10% by weight, calculated from the dry matter. The suspension results are: 1 min) 0.02 ml; 5 min) 0.15 ml; 10 min) 0.25 ml. The average particle size in the suspension is approx. 3 µm.

Example 4

Separate granules containing an activator can be prepared by making from a pre-ground carrier mixture by disc granulation granules which contain:

| | |
|---|---|
| silicic acid (precipitated, e.g. Zeolthix 265) | 85% |
| ammonium sulfate | 2% |
| sodium chloride | 6% |
| lignin sulfonates | 2% |
| phenyl sulfonates | 5% | and by impregnating into it an activator solution (mixture A) which contains:

| | |
|---|---|
| alkyl-sorbitol ethoxylate | 42% |
| fatty alcohol ethoxylate | 21% |
| ethoxylated fatty acid esters | 8% |
| ethoxylated fatty acid phosphate esters | 5% |
| alkylaryl sulfonic acid | 5% |
| alkylamine ethoxylate | 4% |
| paraffin oil | 15% | at the ratio 1:1.5

Separate granules containing an activator may also be mixed to form a single granule mixture with the above-mentioned granule formulations which contain active ingredients, or it can be dispensed separately to form a tank mixture with them. The granules disperse moderately into water.

Example 5

A granular product containing phenmedipham and an activator can be prepared from a raw-material mixture which contains:

| | |
|---|---|
| phenmedipham | 16.0% |
| lignin sulfonates | 2.6% |
| phenyl sulfonates | 5.5% |
| urea | 7.0% |
| kaolin | 5.5% |
| diatomite | 5.0% |
| mixture B | 50.4% |
| polyethylene glycol | 8.0% |

Mixture B contains:

| | |
|---|---|
| silicic acid (precipitated) | 37.5% |
| bentonite | 2.5% |
| fatty alcohol ethoxylates | 16.0% |
| polyoxyethylene sorbitols | 33.8% |
| paraffin oil | 5.1% |
| alkylamine ethoxylates | 5.1% |

The mixture is granulated in a disc in which the mix is heated to +70° C., and the formed granular product is cooled back to room temperature. The suspension properties of the product are moderate.

Example 6

A layered granular product containing phenmedipham and an activator can be prepared from a mixture which contains:

| | |
|---|---|
| phenmedipham | 16.0% |
| lignin sulfonates | 2.7% |
| phenyl sulfonates | 5.3% |
| kaolin | 15.5% |
| diatomite | 5.0% |
| polyethylene glycol | 5.0% |
| mixture B | 50.4% (as in Example 5) |

Mixture B is applied as a coating with the help of polyethylene glycol to a granule prepared from the other raw materials, at +70° C. in a disc granulator. The suspension properties of the granular product are moderate.

Example 7

A granular product containing phenmedipham and an activator can be prepared by the extrusion technique from a raw-material mixture which contains:

| | |
|---|---|
| phenmedipham | 32.0% |
| lignin sulfonates | 7.4% |
| phenyl sulfonates | 2.0% |
| kaolin | 1.1% |
| diatomite | 2.0% |
| naphthene sulfonates | 2.0% |
| mixture C | 50.0% |

Mixture C contains:

| | |
|---|---|
| silicic acid (precipitated) | 34.0% |
| phenyl sulfonates | 0.8% |
| ammonium sulfate | 0.8% |
| sodium chloride | 1.6% |
| lignin sulfonates | 0.8% |
| naphthene sulfonates | 2.0% |
| mixture A | 60.0% |

The suspension properties are: 1 min) 0.15 ml; 5 min) 0.3 ml; 10 min) 0.4 ml.

Example 8

A granular product containing phenmedipham and desmedipham can be prepared from a mixture which contains:

| | |
|---|---|
| phenmedipham | 60.0% |
| desmedipham | 20.0% |
| lignin sulfonates | 5.9% |
| phenyl sulfonates | 5.6% |
| kaolin | 4.0% |
| diatomite | 2.0% |

The suspension properties of the granular product are: 1 min) 0.01 ml; 5 min) 0.02 ml; 10 min) 0.03 ml.

Example 9

A granular product containing phenmedipham and ethofumesate can be prepared by the disc granulation technique from a mixture which contains:

| | |
|---|---|
| phenmedipham | 32.0% |
| ethofumesate | 40.0% |
| lignin sulfonates | 6.0% |
| phenyl sulfonates | 5.0% |
| naphthene sulfonates | 9.0% |
| bentonite | 0.2% |
| urea | 7.8% |

The suspension properties of the granular product are: 1 min) 0.01 ml; 5 min) 0.03 ml; 10 min) 0.04 ml.

Example 9b

Granules containing phenmedipham and ethofumesate can be prepared by disc granulation from a mixture which contains:

| | |
|---|---|
| phenmedipham | 35.0% |
| ethofumesate | 34.7% |
| lignin sulfonates | 5.9% |
| phenyl sulfonates | 5.6% |
| diatomite | 2.0% |
| kaolin | 16.8% |

The suspension properties were: 1 min) 0.15 ml; 5 min) 0.5 ml; 10 min) 0.8 ml.

Example 10

A granular product containing phenmedipham and methamitron can be prepared by disc granulation from a mixture which contains:

| | |
|---|---|
| phenmedipham | 16.0% |
| methamitron | 64.0% |
| lignin sulfonates | 5.9% |
| phenyl sulfonates | 5.6% |
| diatomite | 2.0% |
| kaolin | 6.5% |

The suspension properties of the granular product are: 1 min) 0.01 ml; 5 min) 0.02 ml; 10 min) 0.03 ml.

Example 11

A granular product containing phenmedipham and chlorodazone can be prepared by disc granulation from a mixture which contains:

| | |
|---|---|
| phenmedipham | 25.0% |
| chlorodazone | 50.0% |
| lignin sulfonates | 5.9% |
| phenyl sulfonates | 5.6% |
| diatomite | 1.1% |
| kaolin | 12.4% |

The suspension capacity of the granules is: 1 min) 0.03 ml; 5 min) 0.10 ml; 10 min) 0.15 ml.

Example 11b

A granular product containing phenmedipham and chlorodazone can be prepared by disc granulation from a mixture which contains:

| | |
|---|---|
| phenmedipham | 20.0% |
| chlorodazone | 60.0% |
| lignin sulfonates | 5.9% |
| phenyl sulfonates | 5.6% |
| diatomite | 1.1% |
| kaolin | 7.4% |

The suspension properties of the product are: 1 min) 0.03 ml; 5 min) 0.10 ml; 10 min) 0.15 ml.

Example 12

A granular product containing phenmedipham, desmedipham and chlorodazone can be prepared by disc granulation from a mixture which contains:

| | |
|---|---|
| phenmedipham | 12.0% |
| desmedipham | 3.0% |
| chlorodazone | 45.0% |
| lignin sulfonates | 5.9% |
| phenyl sulfonates | 7.0% |
| fluorinated surfactant | 2.0% |
| alkylaryl betaine | 5.0% |
| diatomite | 1.0% |
| kaolin | 19.1% |

The suspension capacity of the granules is: 1 min) 0.1 ml; 5 min) 0.35 ml; 10 min) 0.45 ml.

Example 13

A tablet containing phenmedipham and an activator can be prepared by compression using a pressure of 300 kg/cm$^2$ from a mixture which contains:

| | |
|---|---|
| phenmedipham | 24.0% |
| lignin sulfonates | 5.9% |
| phenyl sulfonates | 3.0% |
| naphthene sulfonates | 4.5% |
| potassium hydrogenphosphate | 6.0% |
| sodium carbonate | 5.0% |
| magnesium stearate | 1.0% |
| mixture C | 50.0% |
| kaolin | 0.6% |

The tablet can be made in a mold having a diameter of 50 mm, in which case 30 g of mixture is used.

The suspension properties of the tablet are moderate when the dispersion of the tablet in a 500 ml decanter containing 300 ml of water is observed visually.

Biologic Experiments

The activities of the formulations produced were tested in action against weeds commonly encountered in sugar beet cultivation, such as amaranth (*Amaranthus retroflexus*), rape (*Brassica napus*), goosefoot (*Chenopodium album*), and common chickweed (*Stellaria media*). Four pots per weed species per test specimen were used in the experiments. The efficacies were evaluated in accordance with typical evaluation principles on a scale of 0–10, the complete destruction of the plant being described by 10. The mean of four pots was reported.

The sensitivity to injury of the sugar beet (*Beta vulgaris*) was determined on the same scale.

Experiment 1

The biologic efficacy of a mixture of granular phenmedipham (as in Example 1) and a granular activator (as in Example 4) was compared with a phenmedipham-containing emulsion concentrate preparation (Kemifam) available on the market. The amounts of active ingredient in the test specimens were the same, 640 g of active ingredient per hectare. The efficacies were inspected 7 days after the spraying.

| Active ingredient | product/ hectare | Efficacy | | | | |
|---|---|---|---|---|---|---|
| | | ama-ranth | rape | goose-foot | chick-weed | sugar beet |
| Kemifam | 4 l | 5.7 | 7.8 | 9.8 | 7.0 | 1.0 |
| Example 1 | 0.8 kg | 0.7 | 0.0 | 0.0 | 3.0 | 0.0 |
| Example 1 + Example 4 | 0.8 kg 1.5 kg | 4.0 | 8.0 | 8.3 | 7.7 | 0.3 |
| Example 1 + Example 4 | 0.8 kg 3.0 kg | 7.3 | 8.2 | 8.7 | 7.2 | 1.0 |

The result shows that a granular phenmedipham product without an activator is not biologically effective. On the other hand, by means of the granular activator the granular phenmedipham product can be activated so that with the same amount of the product (3.8 kg as compared with 4 l) its action on amaranth, rape and common chickweed is better than that of the reference, and injury to the sugar beet is very little.

Experiment 2

In the experiment, the efficacies of granular products containing phenmedipham and an activator were compared with that of an emulsion concentrate product (Kemifam) available on the market and of a suspension concentrate product (Betaflow) available on the market. The amount of active ingredient per hectare was 640 g/ha in all the experiments. The evaluation was carried out 14 days after the spraying.

| Test product | Efficacy | | | |
|---|---|---|---|---|
| | ama-ranth | rape | chick-weed | sugar beet |
| Kemifam | 4 | 4 | 4 | 1 |
| Betaflow | 4 | 4 | 3 | 1 |
| Example 5 | 3 | 3 | 4 | 1 |
| Example 6 | 4 | 3 | 3 | 1 |

The results show that the granular formulations of phenmedipham have biologic efficacies equal to those of both of the emulsion and suspension concentrate references. The injury to the crop plant is also the same.

Experiment 3

In the experiment, the efficacy of a mixture of a granular product (such as Example 8) containing phenmedipham (69%) and desmedipham (20%) and a granular product (such as Example 4) containing an activator was compared with a commercially available emulsion concentrate preparation containing phenmedipham (129 g/l) and desmedipham (34 g/l). The amounts of active in gredient per hectare were 652 g for Betanal Compact and 640 g for Example 8+Example 4. The efficacies were determined 14 days after the spraying.

| Test product | product/ hectare | Efficacy | | | | |
|---|---|---|---|---|---|---|
| | | ama-ranth | rape | goose-foot | total | sugar beet |
| Betanal Compact | 4 l | 5.5 | 7.2 | 7.0 | 19.7 | 1.0 |
| Example 8 + Example 4 | 0.8 kg 3.8 kg | 8.3 | 5.3 | 9.0 | 22.6 | 1.0 |

The experiment also shows that a mixture of phenmedipham and desmedipham works even better than the corresponding emulsion concentrate product which served as a reference. The injury to sugar beet was the same with both products.

Experiment 4

In the experiment, the efficacy of granules (such as Example 9) containing phenmedipham and ethofumesate and of granules (such as Example 4) containing an activator was compared with that of a commercially available emulsion concentrate product, Betaron, which contains phenmedipham 80 g/l and ethofumesate 100 g/l. The efficacies were determined 14 days after the spraying. The total amount of active ingredients per experiment was 640 g/ha.

| Test product | product/ hectare | Efficacy | | | |
|---|---|---|---|---|---|
| | | ama-ranth | rape | chick-weed | sugar beet |
| Betaron | 3.6 l | 5 | 6 | 9 | 1 |
| Example 9b | 0.81 kg | 4 | 5 | 8 | 1 |
| Example 9b + Example 4 | 0.81 kg 0.67 kg | 8 | 7 | 8 | 1 |

The experiment shows that a granular mixture of phenmedipham and ethofumesate also requires the addition of an activator, whereby a biologically at least equally good result is achieved as with the reference. Injuries caused are identical.

Experiment 5

In the experiment, the efficacies of a granular product containing phenmedipham and methamitron (such as Example 10) and of that product and a granular activator (such as Example 4) were compared with the efficacy of a tank mixture which consisted of a phenmedipham suspension concentrate product which contained active ingredient 160 g/l and of a granular methamitron product (Goltix) having a concentration of 700 g/kg. The amounts of active ingredients per hectare were the same for all the test specimens. The efficacies were determined. 14 days after the spraying.

| Test product | product/ hectare | Efficacy | | | |
|---|---|---|---|---|---|
| | | ama-ranth | rape | chick-weed | sugar beet |
| phenmedipham SC Goltix | 1.5 l 1.37 kg | 9.5 | 9.5 | 10 | 0 |
| Example 10 | 1.5 kg | 7.0 | 7.0 | 9.0 | 0 |

-continued

| Test product | product/ hectare | Efficacy | | | |
|---|---|---|---|---|---|
| | | ama-ranth | rape | chick-weed | sugar beet |
| Example 10 + Example 4 | 1.5 kg 1.1 kg | 7.0 | 9.0 | 9.5 | 0 |

Methamitron, which works both soil-applied and foliage-applied, does not require activators in the same way as does phenmedipham; the relatively high efficacy of granular product 10 is an indication of this. However, even in this case a significant improvement of action on rape is achieved with an addition of activator. Overall, using a granular product of phenmedipham +methamitron+activator, an excellent selective biologic action is achieved without any symptoms of injury in the sugar beet.

Experiment 6

In the experiment, a comparison was made among the efficacies of a granular product containing phenmedipham and chlorodazone, such as Example 11b, in which the concentrations were 20 and 60% respectively, and it and a granular activator, such as Example 4, and a suspension concentrate containing effective phenmedipham and chlorodazone, the concentrations being 100 and 300 g/l. On the other hand, the significance of the granular activator in a triple-mixture granular product which contained phenmedipham, desmedipham and chlorodazone was investigated. The amounts of active ingredient per hectare are the same for all the test specimens. The efficacies were determined 14 days after the spraying

| Test product | product/ hectare | Efficacy | | | |
|---|---|---|---|---|---|
| | | chick-weed | ama-ranth | rape | sugar beet |
| phenmedipham SC chloro-dazone | 4.8 l | 6.0 | 8.0 | 8.0 | 0 |
| Example 11b | 2.4 kg | 5.0 | 4.0 | 3.0 | 0 |
| Example 11b + Example 4 | 2.4 kg 2.3 kg | 6.0 | 6.0 | 7.0 | 0 |
| Example 12 | 3.2 kg | 7.0 | 6.0 | 5.0 | 1.0 |
| Example 12 + Example 4 | 3.2 kg 2.3 kg | 9.0 | 6.0 | 7.5 | 1.0 |

The experiment shows clearly how the increase in efficacy is important also in the mixture formulation of foliage-acting phenmedipham and soil-acting chlorodazone. The same applies to the triple mixture which contains foliage-acting desmedipham in addition to the two former.

Field Experiments

Field experiment 1

The purpose of the experiment was to compare the biologic action of granular products containing phenmedipham to the action of emulsion and suspension concentrate products already available commercially.

The experiments were conducted in accordance with conventional field experiment practices. There were three rounds of application, all performed after the emergence of seedlings of sugar beet. The efficacy was examined visually and evaluated in relation to an untreated plant stand, the value for which was 0. Value 100 describes complete control capacity. The amount of phenmedipham used in each round of spraying was 480 g/ha.

| Test product | product/ha | efficacy % |
|---|---|---|
| 1 Kemifam (phenmedipham 160 g/l, EC) | 3 * 3 l | 75 |
| 2 Batanal Plus (phenmedipham 160 g/l, SC) | 3 * 3 l | 83 |
| 3 Example 1 Example 4 | 3 * 0.6 kg 3 * 1.15 kg | 83 |
| 4 Example 1 Example 4 | 3 * 0.6 kg 3 * 2.3 kg | 93 |
| 5 Example 1 Example 4 mixture A | 3 * 0.6 kg 3 * 1.4 kg | 83 |
| 6 Example 7 | 3 * 1.5 kg | 55 |
| 7 Example 7 Example 4 | 3 * 1.5 kg 3 * 1.15 kg | 81 |

The efficacy of the granular product containing an active ingredient, used together with a granular activator, the total amount of the material used being 1.75 kg/ha, is as good as the efficacy of the suspension product when used at 3 l/ha. When a granular product containing more activator was used, in which case the total amount of material used is 2.75 kg/ha, a significantly better efficacy is obtained with the granular product than with the suspension product. In the experiment, the granules containing activator were dispensed separately for reasons of test-performing techniques, but it is clear that a granular mix containing an active ingredient and an activator can be mixed in advance to form a single homogenous mix to be dispensed as one.

Together with a granular product which contains active ingredient it is possible to use a liquid activator in the conventional manner as a tank mixture, as in test specimen 5. The activator granules of Example 4 contain mixture A 60%, in which case test specimens 4 and 5 contain equal amounts of the liquid ingredient. However, it can be observed surprisingly that the solid carrier material of the granular product increases the effect of the activator granules on the efficacy of the active ingredient by up to 10%. It is also noteworthy that this granular product is more than 10% more effective than the commercial suspension concentrate product and up to 20% more effective than the commercial emulsion concentrate product.

Field Experiment 2

In the experiment, the biologic efficacy of a granular product containing phenmedipham and ethofumesate (Example 9a) and an activator (Example 4) was compared with the efficacy of an emulsion concentrate product (Betaron) available on the market. The overall test arrangements were as in field experiment 1. The amount of active ingredient used was 540 g per ha per spraying round.

| Test product | product/ha | efficacy % |
|---|---|---|
| 1 Betaron phenmedipham 80 g/l ethofumesate 100 g/l | 3 * 3 l | 95 |
| 2 Example 9 a Example 4 | 3 * 0.75 kg 3 * 0.58 kg | 91 |
| 3 Example 9 a Example 4 | 3 * 0.75 kg 3 * 1.15 kg | 93 |

With a total amount of 1.33 kg of the granular product, almost the same efficacy was obtained as with 3 l of the emulsion concentrate. The handling of the product containing an active ingredient and an activator in connection with the spraying did not cause difficulties.

Field Experiment 3

In the experiment, the efficacies of a conventional spraying program used in the cultivation of sugar beet and a spraying program based on granules were compared. In practice, phenmedipham, methamitron or ethofumesate is not generally used alone, but tank mixtures of these are used, in which the mixing ratios may vary, depending on the weeds.

Kemiron is an emulsion concentrate containing ethofumesate 200 g per liter, and granular ethofumesate (EFU granule) is a water dispersible granular product containing effective ingredient 65%. The amounts of active ingredient per hectare were the same with both the test specimens.

Conventional Program
  1st spraying 1.5 l Kemifam+1 kg Goltix+0.5 l Kemiron
  2nd spraying 1.5 l Kemifam+1 kg Goltix+1.0 l Kemiron
  3rd spraying 1.5 l Kemifam+0.5 kg Goltix+1.0 l Kemiron Program Based on Granules
  1st spraying 0.2 kg Example 1+1 kg Goltix+1.15 kg EFU-granules
  2nd spraying 0.2 kg Example 1+1 kg Goltix+0.3 kg EFU-granules
  3rd spraying 0.2 kg Example 1+0.5 kg Goltix+0.3 kg EFU-granules
each spraying containing 1.15 kg Example 4

| Efficacies: | conventional program | 90% |
| --- | --- | --- |
|  | granule-based program | 89% |

The results show that the program based on granular products has worked as well as has the program in which phenmedipham and ethofumesate are in liquid form as emulsion-emulsion concentrates.

We claim:

1. A method for the preparation of herbicidal product in granular form,
  said product comprising a herbicidally effective compound comprising at least one member of the group consisting of methyl-3-m-tolyl-carbamoyloxyphenylcarbamate and ethyl-e-phenyl-carbamoyloxyphenylcarbamate, and an activator ingredient comprising at least one of the group consisting of surfactants and oils,
  said method comprising the steps of:
    (A) combining the activator ingredient with a solid carrier material to form a solid activator composition; and
    (B) combining the solid activator composition with the herbicidally effective compound to form said herbicidal product wherein said activator composition and said herbicidally effective compound are separated into two different solid phases, the phase containing said activator composition being substantially free of said herbicidally effective compound and the phase containing said herbicidally effective compound being substantially free of said activator composition, said activator composition and said herbicidally effective compound being combined by:
      (a) forming granules comprising the herbicidally effective compound and covering the granules with a layer of the solid activator composition; or
      (b) forming granules comprising the solid activator composition and covering the granules with a solid layer comprising the herbicidally effective compound; or
      (c) forming first granules comprising the herbicidally effective compound and forming second granules comprising the solid activator composition, said steps of forming said first and second granules each comprising the steps of finely dividing said herbicidally effective compound or said solid activator composition, respectively, by comminuting and granulating said finely divided herbicidally effective compound or said solid activator composition to form said first and second granules, respectively, and mixing together the first and second granules.

2. A method according to claim 1, wherein the activator ingredient is a liquid, and said activator ingredient is impregnated into the solid carrier material to form said activator composition.

3. A method according to claim 1, wherein the activator ingredient is a solid and said activator ingredient is mixed with the solid carrier material to form said activator composition.

4. A method according to claim 1, wherein the carrier material is of natural origin.

5. A method according to claim 1, wherein the carrier material is a synthetic material.

6. A method according to claim 1, wherein the activator ingredient comprises at least one member of the group consisting of anionic surfactants, cationic surfactants, amphoteric surfactants, and non-ionic surfactants.

7. A method according to claim 1, wherein the activator ingredient comprises at least one member of the group consisting of mineral oils, vegetable oils, animal oils, hydrolyzed mineral oils, hydrolyzed vegetable oils, and hydrolyzed animal oils.

8. A method according to claim 1, wherein the activator ingredient comprises approximately 50–100% surfactant(s).

9. A method according to claim 1, wherein the activator ingredient comprises oil in an amount of up to 50% of said activator ingredient.

10. A method according to claim 1, wherein the activator ingredient comprises approximately 10–70% of the solid activator composition.

11. A method according to claim 1, wherein the solid activator composition comprises an auxiliary agent contained in the solid activator composition for dispersing, wetting, granulating, stabilizing, pH control, or defoaming the activator composition.

12. A method according to claim 1, wherein the herbicidal product further comprises a plant protection agent comprising at least one member of the group consisting of chlorodazone, methamitron, and ethofumesate.

13. A method according to claim 12, wherein said plant protection agent is incorporated in said herbicidal product in the same granules as said herbicidally effective compound.

14. A method according to claim 12, wherein said plant protection agent is incorporated in said herbicidal product in granules separate from granules containing said herbicidally effective compound.

15. A method for the preparation of herbicidal product in granular form,
  said product comprising a herbicidally effective compound comprising at least one member of the group consisting of methy-3-m-toly-carbamoyloxyphenylcarbamate and ethyl-e-carbamoyloxyphenylcarbamate, and an activator ingredient comprising at least one of the group consisting of surfactants and oils, said surfactant(s) being selected from the group consisting of alkyl sulfonates, alkylaryl sulfonates, sulfate ethers, fatty alcohol sulfates, sulfate esters, sulfocarboxylic acids and their derivatives, alkylglycerolether sulfonates, sulfoesters, sulfonamides, phosphoric acid mono- and diesters, bile acids and their salts, alkylamines, alkylarylamines, alkyl imidazolines, alkylaryl imidazolines, alkylaminoamides, fatty alcohol ethoxylates, fatty acid ethoxylates, alkylaryl ethoxylates, alkyl sugar ethyoxylates, alkyl sugar alcohol ethoxylates, alkylamine polyglycol ethers, alkylarylamine polyglycol ethers, fatty acid amide derivatives, diethanolamides of fatty acids, polydiethanolamides of fatty acids, derivatives of mono-, di-, and triglycerides, acetylene diols, silicon-based surfactants, alkyl betaine derivatives, alkylaryl betaine derivatives, alkyl (poly)glycine derivatives, alkylaryl (poly)glycine derivatives, alkylamide carboxylates, alkylarylamide carboxylates, alkylamine sulfonates, alkylarylamine sulfonates, and fluorine-containing surfactants;

said method comprising the steps of:

(A) combining the activator ingredient with a solid carrier material to form a solid activator composition; and (B) combining the solid activator composition with the herbicidally effective compound to form said herbicidal product wherein said activator composition and said herbicidally effective compound are separated into two different solid phases, the phase containing said activator composition being substantially free of said herbicidally effective compound and the phase containing said herbicidally effective compound being substantially free of said activator composition, said activator composition and said herbicidally effective compound being combined by:

(a) forming granules comprising the herbicidally effective compound and covering the granules with a layer of the solid activator composition; or (b) forming granules comprising the solid activator composition and covering the granules with a solid layer comprising the herbicidally effective compound; or (c) forming first granules comprising the herbicidally effective compound and forming second granules comprising the solid activator composition, said steps of forming said first and second granules each comprising the steps of finely dividing said herbicidally effective compound of said solid activator composition respectively, by comminuting and granulating said finely divided herbicidally effective compound or said solid activator composition to form said first and second granules, respectively, and mixing together the first and second granules.

16. A method for the preparation of herbicidal product in granular form, said product comprising a herbicidally effective compound comprising at least one member of the group consisting of methyl-3-m-tolyl-carbamoyloxyphenylcarbamate and ethyl-e-phenyl-carbomoyloxyphenylcarbamate, and an activator ingredient comprising at least one of the group consisting of surfactants and oils, said method comprising the steps of:

(A) combining the activator ingredient with a solid carrier material for form a solid activator composition; and (B) combining the solid activator composition with the herbicidally effective compound to form said herbicidal product wherein said activator composition and said herbicidally effective compound are separated into two different solid phases, the phase containing said activator composition being free of an effective amount of said herbicidally effective compound and the phase containing said herbicidally effective compound being free of an effective amount of said activator composition, said activator composition and said herbicidally effective compound being combined by:

(a) forming granules comprising the herbicidally effective compound and covering the granules with a layer of the solid activator composition; or (b) forming granules comprising the solid activator composition and covering the granules with a solid layer comprising the herbicidally effective compound; or (c) forming first granules comprising the herbicidally effective compound and forming second granules comprising the solid activator composition, said steps of forming said first and second granules each comprising the steps of finely dividing said herbicidally effective compound or said solid activator composition, respectively, by comminuting and granulating said finely divided herbicidally effective compound or said solid activator composition to form said first and second granules, respectively, and mixing together the first and second granules.

\* \* \* \* \*